US008986385B2

(12) United States Patent
Hall

(10) Patent No.: US 8,986,385 B2
(45) Date of Patent: *Mar. 24, 2015

(54) NESTED EXPANDABLE SLEEVE IMPLANT

(71) Applicant: DePuy Synthes Products, LLC, Raynham, MA (US)

(72) Inventor: Harry Thomas Hall, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/082,275

(22) Filed: Nov. 18, 2013

(65) Prior Publication Data
US 2014/0081401 A1 Mar. 20, 2014

Related U.S. Application Data

(63) Continuation of application No. 12/921,698, filed as application No. PCT/US2009/036659 on Mar. 10, 2009, now Pat. No. 8,585,762.

(60) Provisional application No. 61/036,766, filed on Mar. 14, 2008.

(51) Int. Cl.
*A61F 2/44* (2006.01)
*A61B 17/68* (2006.01)
*A61B 17/88* (2006.01)

(52) U.S. Cl.
CPC . *A61F 2/44* (2013.01); *A61B 17/68* (2013.01); *A61B 17/8858* (2013.01); *Y10S 623/902* (2013.01)
USPC ........ 623/17.11; 606/279; 606/86 A; 623/902

(58) Field of Classification Search
CPC .......................... A61M 25/04; A61M 25/0074
USPC .......... 600/184; 606/86 A, 279, 86 R, 95.99, 606/100, 191–199; 623/17.11–17.16, 1.16, 623/16.11, 23.48, 23.63, 23.51–23.55; 604/104–109
See application file for complete search history.

(56) References Cited

U.S. PATENT DOCUMENTS

| 4,716,901 | A | * | 1/1988 | Jackson et al. | ................ | 606/185 |
| 5,176,659 | A | * | 1/1993 | Mancini | ....................... | 604/523 |

(Continued)

FOREIGN PATENT DOCUMENTS

| EP | 1844714 | 10/2007 |
| JP | 2004/525692 | 8/2004 |

(Continued)

OTHER PUBLICATIONS

Japanese Patent Application No. 2010-550814: Office Action dated Oct. 30, 2013, 5 pages.

*Primary Examiner* — Todd Manahan
*Assistant Examiner* — Marcela I Shirsat
(74) *Attorney, Agent, or Firm* — Baker & Hostetler LLP

(57) ABSTRACT

An expandable implant for treating bone preferably in a minimally invasive manner includes a preferably cylindrical core element extending along a longitudinal axis and preferably a plurality of nestable, expandable sleeves extending along a longitudinal axis for placement radially about the core element. The plurality of nestable sleeves are sequentially insertable over the core element in such a manner that a first nestable sleeve is inserted over the core element and each subsequently inserted nestable sleeve is received between the core element and the previously inserted nestable sleeve such that the insertion of each additional sleeve causes each previously inserted sleeve to outwardly expand.

20 Claims, 6 Drawing Sheets

(56) References Cited

U.S. PATENT DOCUMENTS

| | | | |
|---|---|---|---|
| 5,183,464 A | 2/1993 | Dubrul et al. | |
| 5,573,517 A * | 11/1996 | Bonutti et al. | 604/264 |
| 6,162,236 A * | 12/2000 | Osada | 606/185 |
| 6,186,986 B1 * | 2/2001 | Berg et al. | 604/264 |
| 6,245,101 B1 | 6/2001 | Drasler et al. | |
| 6,325,823 B1 | 12/2001 | Horzewski et al. | |
| 6,752,825 B2 | 6/2004 | Eskuri | |
| 7,811,303 B2 | 10/2010 | Fallin et al. | |
| 8,016,873 B1 | 9/2011 | Drasler et al. | |
| 8,034,109 B2 * | 10/2011 | Zwirkoski | 623/17.11 |
| 8,328,852 B2 * | 12/2012 | Zehavi et al. | 606/279 |
| 8,585,762 B2 * | 11/2013 | Hall | 623/17.11 |
| 2005/0182436 A1 * | 8/2005 | Chopra | 606/192 |
| 2005/0288763 A1 * | 12/2005 | Andreas et al. | 623/1.11 |
| 2006/0089715 A1 | 4/2006 | Truckai et al. | |
| 2006/0217754 A1 | 9/2006 | Boehm et al. | |
| 2006/0282147 A1 | 12/2006 | Andreas | |
| 2007/0093899 A1 | 4/2007 | Dutoit et al. | |

FOREIGN PATENT DOCUMENTS

| | | |
|---|---|---|
| WO | WO 02/071921 | 9/2002 |
| WO | WO 2009/114523 | 9/2009 |

\* cited by examiner

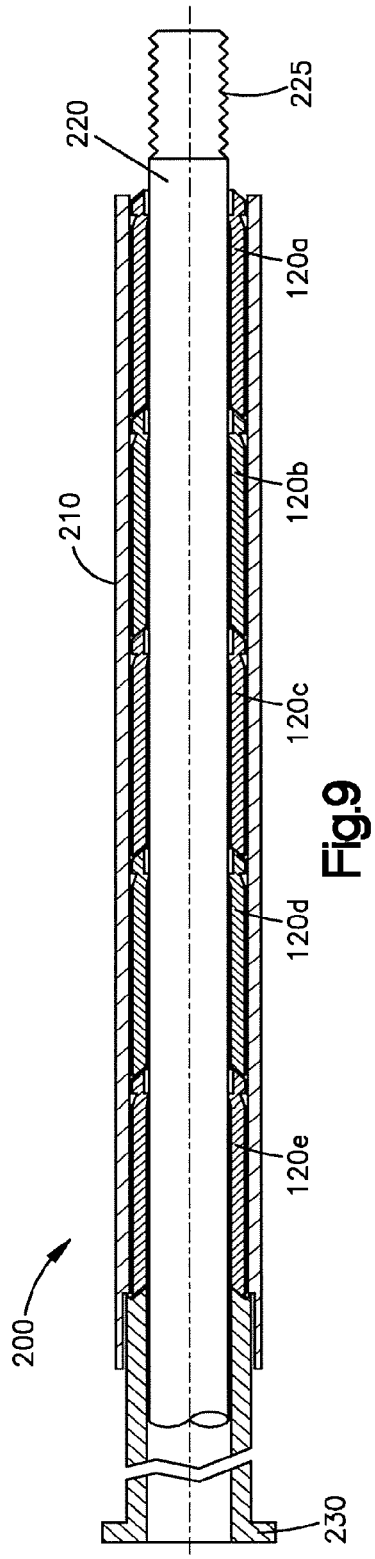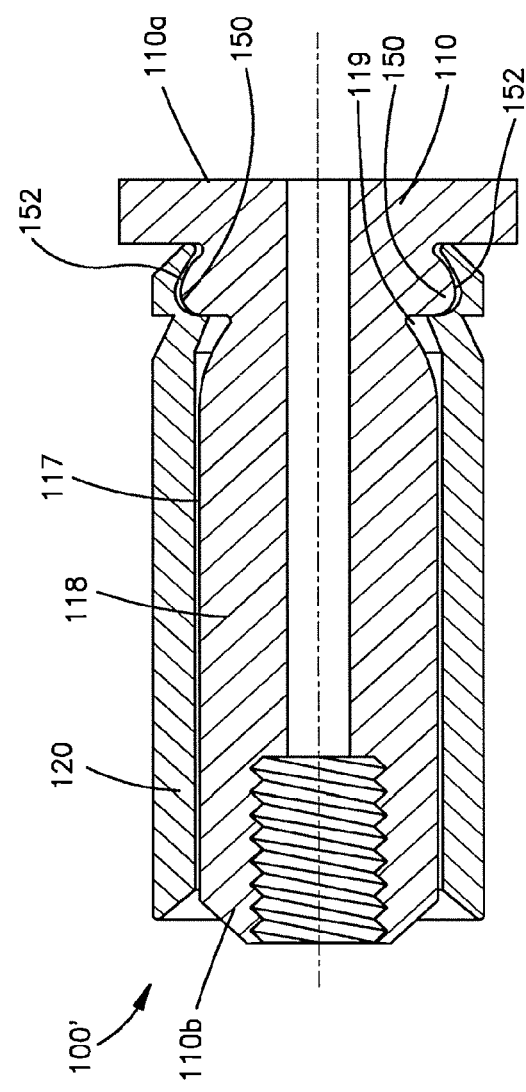

NESTED EXPANDABLE SLEEVE IMPLANT

CROSS REFERENCE TO RELATED APPLICATIONS

This application is a continuation of U.S. patent application Ser. No. 12/921,698, filed Sep. 9, 2010, which is the National State of International Application No. PCT/US2009/036659, filed Mar. 10, 2009, which claims the benefit of U.S. Provisional Application No. 61,036,766, filed Mar. 14, 2008, the contents of which are hereby incorporated by reference as if set forth in their entireties herein.

TECHNICAL FIELD

The present application relates generally to orthopedics, and more specifically, to bone augmentation using expandable bone augmentation implantation devices. The device of the present application may be appropriate for use in minimally invasive surgical techniques, and in particular for use in vertebra, long bones, etc.

BACKGROUND

As bone ages the cancellous bone tends to become less dense and more osteoporotic. As bone becomes less dense and more osteoporotic it is more prone to fractures, collapse and being unable to support loads. To strengthen such bone, methods, instruments, implants and devices have been developed to augment and strengthen bone. These devices however have shortcomings Most compression fracture fixation devices are inflatable, such as balloon expandable devices used in vertebralplasty. Such methods, instruments, devices and implants include no way of centering a load bearing element(s) and centrally applying an expansion mechanism to keep the axis intact. Also absent in known methods, instruments, devices and implants is a structural support for such devices other than hydraulic pressure. It would be advantageous to construct a percutaneous bone augmentation solution that provides both structural support as well as a concentrically applied expansion.

SUMMARY

In one embodiment, the present invention is directed to an expandable implant preferably for treating bone in a minimally invasive manner. The implant may comprise a core element extending along a longitudinal axis, and one or more of sleeves, preferably a plurality of sleeves, placed radially about the core element. The sleeves may be nestable and expandable. The plurality of sleeves may be sequentially insertable over the core element in such a manner that a first sleeve is inserted over the core element and each subsequently inserted sleeve is received between the core element and the previously inserted sleeve such that the insertion of each additional sleeve causes each previously inserted sleeve to outwardly expand. The expandable implant and/or core element may be substantially cylindrically shaped, or comprise other shapes that may have at least one flat surface or side, such as, for example, a hexagon, square, octagon, trapezoid or other polygonal shapes. The expandable implant may also be asymmetrically shaped or alternatively symmetrically shaped.

The expandable implant may further comprise an expandable membrane to provide radial compression to the expandable sleeves. The sleeves may comprise ribs and spacers. The sleeves, for example may extend circumferentially about a central axis to form a hollow cylinder or tube. Alternatively, the ribs, spacers or other structural elements forming the sleeve may extend less than the entire circumference about the longitudinal axis so that the resultant expandable implant may be asymmetrical about its axis. The sleeves, and structural elements forming the sleeve, may comprise a one piece integral unit formed of ribs and spacers connected by flexible struts. The sleeves and/or expandable implant in its expanded condition may be cylindrically shaped, or the implant may form at least one flat surface or side, as would result from an implant forming, for example, a substantially hexagonal, square, trapezoidal, octagonal or other polygonal shaped implant.

The core element and sleeves of the expandable implant may be substantially the same length, or preferably the sleeves will be slightly shorter in length than the core element. The sleeves and core element may have at least one of a projection and recess so that the sleeves interdigitate with each other and the core element. The inside diameter or cross-sectional shape of the expandable sleeve in the unexpanded natural state may be slightly less than the diameter or cross sectional shape and size of the proximal end of the core element. Such a configuration may permit the sleeve to expand slightly as it is fitted over the core element which may assist in securing the sleeve in position on the implant.

In another embodiment the present invention may comprise a kit comprising one or more core elements having a longitudinal axis, and one or more sleeves for placement radially about the core element, wherein the sleeves are sized and configured to be sequentially insertable over the core element in such a manner that a first sleeve is inserted over the core element and each subsequentially inserted sleeve is inserted between the core element and the previously inserted sleeve such that the insertion of each additional sleeve causes each previously inserted sleeve to outwardly expand. The core element has a distal end and a proximal end, and the sleeves have a distal end and a proximal end, wherein the distal end of the sleeve is configured and sized to be inserted first over the proximal end of the core element and moved over the core element so that the proximal end of the sleeve is substantially aligned with the proximal end of the core element, preferably while the core element, and or core element and previously placed sleeves, are positioned within bone. The sleeves are preferably nestable and radially expandable, and preferably interlock with each other and/or the core element.

In another embodiment the present invention may comprise a system or kit for treating bone preferably in a minimally invasive manner, the system including (i) providing a core element having a length extending along a longitudinal axis and further including a proximal end, a distal end and an instrument engagement feature at the proximal end; (ii) providing an insertion instrument that includes a cannulated barrel, a rod element located within the cannulated barrel, the rod element including a core element engagement feature at the distal end; and (iii) one or more sleeve elements, preferably nestable and expandable sleeve elements positionable along the exterior of the rod element in end-to-end fashion and within the cannulated barrel, wherein the instrument engagement feature of the proximal end of the core element is engageable to the core element engagement feature at the distal end of the rod element, and wherein the sleeve elements from within the cannulated barrel are advanceable along the rod element and over the core element, whereby advancing at least one additional sleeve element from within the cannulated barrel along the rod element and between the core element and the previously inserted sleeve element causes the radial expansion of the previously inserted sleeve element, wherein the radius of the implant expands as each additional sleeve element is applied about the core element.

Both the core and sleeve elements may be provided in a variety of lengths. For example, a number of core elements of different length may be provided, and a number of insertion instruments containing different length sleeve elements corresponding to the different length core elements may be provided. The core and sleeve elements may, for example, start at 2 cm lengths and increase in increments of 2 mm to provide an assortment of sizes for the surgeon to choose from during a surgical procedure. Each insertion instrument may have more than a sufficient number of sleeve elements so that the surgeon can custom tailor the size (diameter, cross-sectional size, girth or thickness) of the implant during the surgical procedure. Each insertion instrument may have a different or the same number of sleeve elements provided, and a surgeon may be able to load the sleeve elements into the insertion instrument prior to surgery based upon the sizing requirements for the particular procedure anticipated. Alterations in the number and size of the sleeve elements loaded into the insertion instrument may be accommodated during the procedure.

A method of treating bone in a minimally invasive manner is also described. The method may include one or more of the following steps: (a) forming an access path to a bone to be treated, for example, a vertebral body; (b) providing a core element having a length extending along a longitudinal axis and further including a proximal end, a distal end and an instrument engagement feature at the proximal end; (c) providing an insertion instrument that includes a cannulated barrel, a rod element located within the cannulated barrel, and one or more sleeve elements, preferably nestable and expandable sleeve elements, the rod element further including a core element engagement feature at the distal end, wherein the plurality of sleeve elements are disposed in end-to-end fashion along the rod element and within the cannulated barrel; (d) engaging or attaching the instrument engagement feature at the proximal end of the core element to the core element engagement feature at the distal end of the rod element; (e) inserting the core element through the access path and into the bone to be treated; (f) advancing a sleeve element from within the cannulated barrel along the rod element and over the core element; (g) preferably advancing at least one additional sleeve element from within the cannulated barrel along the rod element and between the core element and the previously inserted sleeve element, thereby causing the radial expansion of the previously inserted sleeve element, wherein the radius of the implant expands as each additional sleeve element is applied about the core element; (h) disengaging the insertion instrument from the core element; and (i) removing the insertion instrument from the patient to be treated. In the method of treating bone, the core element may be placed in the bone to be treated and thereafter the insertion instrument may be attached to the core element, or the core element and insertion instrument first may be attached to each other and the assembly placed in the patient together, with the core element placed in the bone to be treated and the proximal end of the insertion instrument extending from the patient.

In another embodiment an expandable implant for treating tissue preferably in a minimally invasive manner is provided, the implant includes a preferably cylindrical core element extending along a longitudinal axis and preferably a plurality of nestable, expandable sleeves extending along a longitudinal axis for placement radially about the core element. The plurality of nestable sleeves are sequentially insertable over the core element in such a manner that a first nestable sleeve is inserted over the core element and each subsequently inserted nestable sleeve is received between the core element and the previously inserted nestable sleeve such that the insertion of each additional sleeve causes each previously inserted sleeve to outwardly expand.

The implant, system, kit and method may be applied to any number of bones and bone conditions and treatments and even as preventative measures to prevent bone compression or fractures. For example the implant, system, kit and method may be applied to treat vertebral compression fractures or metaphyseal fractures in long bones, or to treat other bones, or for non-medical applications. The implant, system, kit and method may be used to fill voids or cavities created in bone or other tissue, and may be used to compact cancellous bone to form and fill a cavity in the bone, and may be used to move bone, for example, cortical bone, including but not limited to vertebral endplates to restore vertebral height and angle.

BRIEF DESCRIPTION OF THE DRAWINGS

The foregoing summary, as well as the following detailed description of preferred embodiments of the application, will be better understood when read in conjunction with the appended drawings. The drawings, examples and embodiments described within this specification are for the purposes of describing and enabling the expandable implant system, kit and method of use, and are to be understood as illustrative and exemplary of structures, features, aspects and methods of using the present invention, and not as limiting the scope of the invention. It should be understood that the application is not limited to the precise arrangements, configurations and instrumentalities shown. In the drawings:

FIG. 9 illustrates a cross sectional view of an insertion instrument with a plurality of expandable sleeves mounted therein;

FIG. 10 illustrates a cross-sectional view of another embodiment of an expandable implant in accordance with the present invention;

DETAILED DESCRIPTION OF ILLUSTRATIVE EMBODIMENTS

Figure 1:
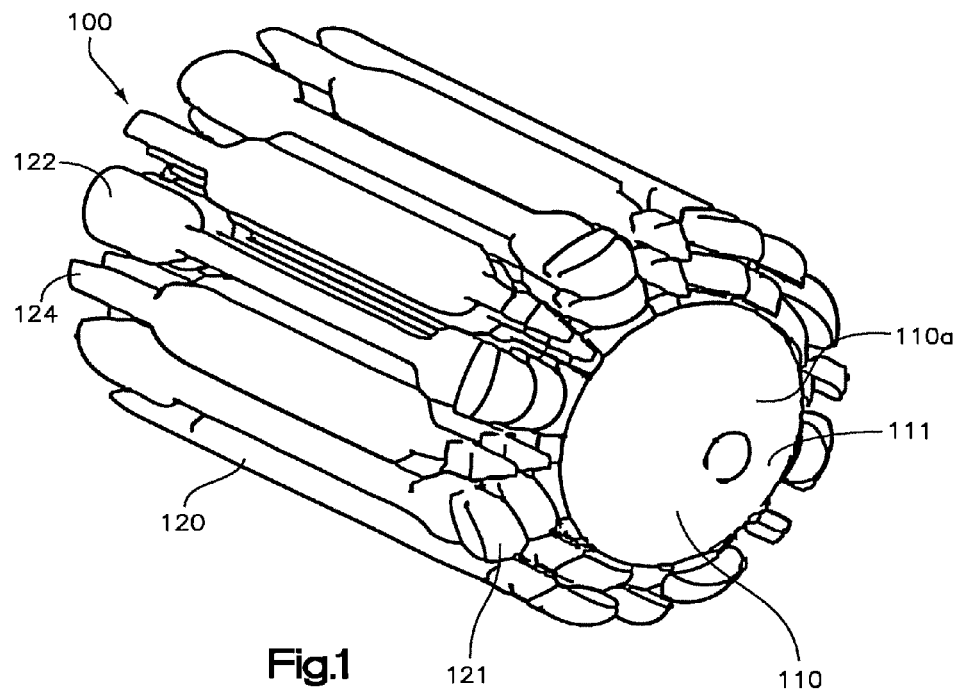
FIG. 1 illustrates a front top perspective view of an expandable implant in accordance with the present invention.
Figure 2:
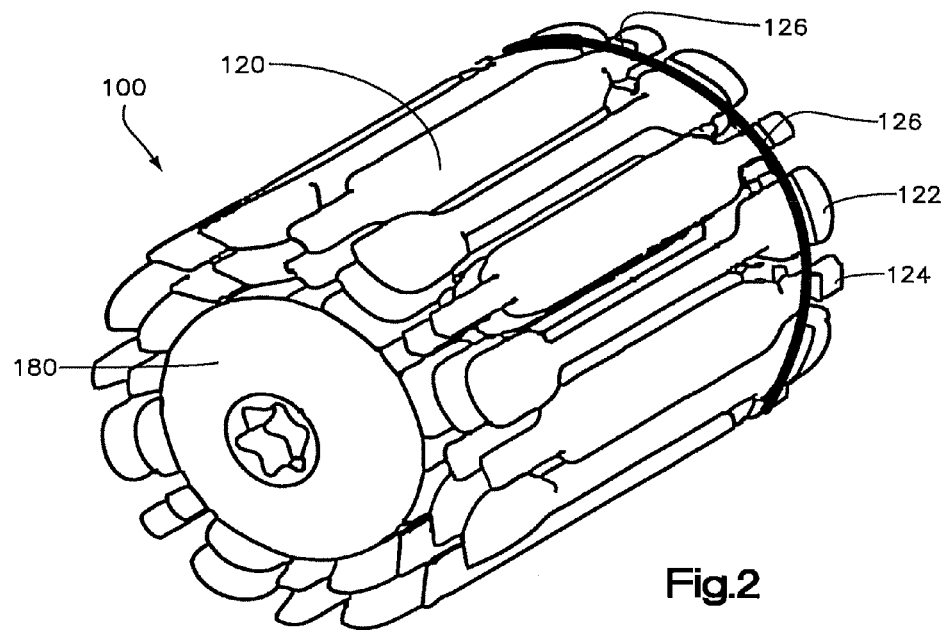
FIG. 2 illustrates a back top perspective view of the expandable implant of FIG. 1.
Figure 3:
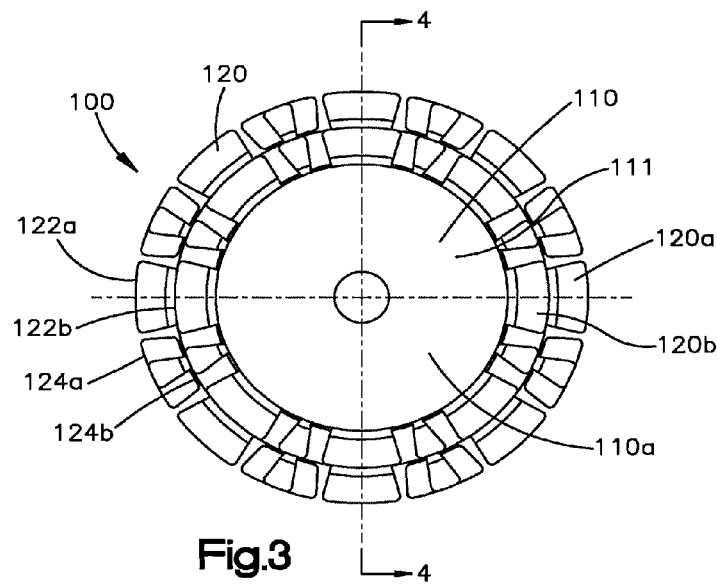
FIG. 3 illustrates a front elevational view of the expandable implant of FIG. 1.

The embodiments implants, systems, kits, methods, and examples described within this specification are to be understood as illustrative and exemplary of the structures, features and aspects of the implants, systems, kits and methods of the present invention, and not as limiting the scope of the invention. The features, structures, aspects and steps of the implant, system and method may be used singularly, alternatively or together as desired or appropriate. Certain terminology used in the following description is for convenience and description only and is not be used in a limiting manner or to be limiting in nature. The words "right", "left", "lower" and "upper" designate directions in the drawings to which reference is made. The words "inwardly" and "outwardly" refer to directions toward and away from, respectively, the geometric center of the device and designated parts thereof The words, "anterior", "posterior", "superior", "inferior" and related words and/or phrases designate preferred positions and orientations in the human body to which reference is made and are not meant to be limiting in nature. The terminology includes the above-listed words, derivatives thereof and words of similar import.

In accordance with the present invention, and in reference to FIGS. 1-4, an expandable bone augmentation implant 100 is provided. The implant 100 preferably includes a core element 110, in this embodiment more preferably a substantially cylindrical core element, capable of being inserted into a bony void such as, for example, within a compression fracture of the metaphyseal portion of a long bone, vertebral compression fracture, etc., and preferably will provide structural support to the bone or other tissue in which it is implanted. The core element 110 may be solid or cannulated and has a longitudinal axis 112. The lumen or bore 118 may extend partially or completely down the length of the core element 110. A full length cannulation may permit and facilitate placement of the core element and implant into position over a guide wire. In a preferred embodiment, the core element 110 includes a bullet-nosed, rounded, or otherwise contoured tip 111 at its distal end 110a. The proximal end 110b of the core element 110 preferably includes an instrument engagement feature 115, such as a length of threading on the core element 110, for example, a length of threading 112 along the proximal portion 118a of the interior bore 118, to enable ease of insertion. Alternatively, or additionally, the proximal portion 118a of the interior bore 118 may be sized and shaped to receive a projection on the insertion instrument in a snap fit, or the core element may attach to the insertion instrument by other attachment means. Alternatively, the instrument engagement feature 115 may assume alternative forms, such as a feature (not shown) on the exterior surface 117 of the core element 110.

The implant core element is preferably formed from a material of sufficient structural integrity to support physiological loads that will be applied to the bone or tissue to be treated. The thickness, configuration and material of the core element will depend upon the bone or tissue to be treated, the location of the implant within the bone or tissue to be treated, the size of the patient and the forces that may be applied to the implant in use. Suitable materials for the core element may be titanium, titanium alloys, stainless steel, ceramics, composite materials, polymers, PEEK and/or other biocompatible materials.

The implant 100 preferably includes one or more sleeve elements 120 so that, in use, the implant 100 is preferably radially expandable by sequentially inserting sleeve elements 120 that stack or nest around the implant core element 110. Preferably the sleeve elements are radially expandable. As shown, a first sleeve 120a may be slid over the core element 110 using an insertion instrument, such as, inserter instrument 200, as is discussed in detail below. A second sleeve 120b may be slid over the core element 110 between the previously inserted sleeve element 120a and the core element 110 such that as the second sleeve 120b is inserted between the core element 110 and the first sleeve 120a, the first sleeve 120a expands radially. As a third sleeve element 120c is slid over the core element 110 between the second sleeve element 120b and the core element 110, the first and second sleeves 120a, 120b radially expand. Any number of sleeve elements 120 can be chosen to provide the desired final shape and size of the implant 100. As a result, the implant 100 provides a preferably, structurally rigid implant 100 preferably capable of insertion through a percutaneous access path utilizing a preferably minimally invasive procedure and which undergoes incremental expansion to a larger implant volume to thereby fill a void or cavity in bone or tissue, and preferably support the loads applied across the bone or tissue, act as supplemental fixation for other hardware or implants, such as, for example, screws or other fasteners, as well as, in some cases, restore the desired height and shape of a collapsed bone or tissue, for example a collapsed vertebral body. The expansion of the implant may compact cancellous bone, and may restore the height and shape of a collapsed bone by moving the cortical bone.

The structure and configuration of the core element 110 will be described in more detail as will the sleeve element and the interaction between the core element 110 and sleeve element 120 to form the expandable implant 100. While the core element 118 in the embodiment of FIGS. 1-5 has been shown and described as being substantially cylindrical in shape and having a diameter and a length, it is to be understood that the cross sectional shape of the core element may be non-circular, and may have a cross-sectional shape that provides a flat surface or side, such as, for example, a square, hexagon, octagon, trapezoid or other polygon shape. These and other shapes are contemplated for use for the core element. The term "diameter" when used when referring to a non-circular cross-section refers to the cross-sectional size, width and thickness as may be appropriate in the given context.

Figure 5:
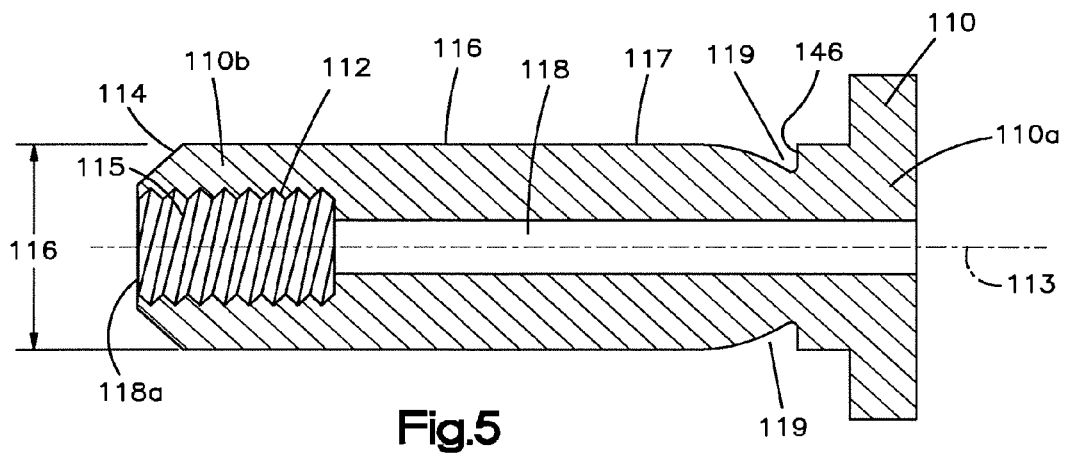
FIG. 5 illustrates a cross sectional view of the core element of the expandable implant shown in FIGS. 1-4.

The core element may have a first diameter 116 or cross-sectional shape along a substantial portion of its length. The proximal end 110b of the core element may have a beveled, chamfered or blunt edge 114 to facilitate sliding of the sleeve elements onto the core element. The distal end 110a of the core element 110 may be enlarged to form a stop 111a for one or more of sleeve elements 120. The core element 110 may be provided with one or more recesses 119 on its exterior surface 117. The recesses 119 permit and facilitate engaging and securing the sleeve elements 120 to the core element 110 as will be described in more detail below. The recesses 119 may be provided circumferentially around the exterior surface 117 of the core element, or at select locations along the circumference of the exterior surface 117 of the core element. Recesses 119 may be provided on the distal portion as illustrated in FIG. 5, or alternatively, or in addition to, at the proximal or middle portions of the core element 110. Recesses 119 may include other features and configurations to permit and facilitate the engagement and securing of the sleeve elements on the core element.

The core element may further include one or more expandable bands 136 (not shown) that extend circumferentially around the core element. Expandable bands 136 may extend around the proximal, middle and/or distal portions of the core element 110. The expandable bands 136 may assist in providing a radial compression force against the sleeve elements 120 as the sleeve elements are slid into position on the core element 110. The sleeve element 120 preferably would be positioned under the expandable bands 136. In addition, the core element may include one or more longitudinal grooves (not shown) to assist and facilitate the positioning and orientation of the sleeve elements as they move over the core element.

The core element 110 preferably is sized and shaped to permit and facilitate insertion into bone through a minimally invasive opening, such as, for example, through a puncture, cannula or small incision. In one embodiment, the outside diameter of the core element may be approximately 6 mm, with the distal tip 110a being approximately 8 mm in diameter. Other diameters and configurations of the core element are contemplated. The core element 110a may be provided in a variety of sizes, for example, a plurality of different lengths and/or diameters, and/or cross-sectional shapes, appropriate for the different bones intended to be treated. In one embodiment, the core element may have a length of approximately 2 centimeters long. Numerous core elements may be provided in different lengths so that an implant 100 appropriate for the bone to be treated can be assembled via components provided in a kit, or can be assembled in the operating room as part of a system to form an appropriate size implant. The different size core elements can be provided in lengths that increase in preselected increments, such as, for example, 2 mm, so that the core elements may be 2 cm, 2.2 cm, 2.4 cm, 2.6 cm, etc., in length. In this manner, the appropriate length implant can be selected for the bone to be treated. The diameter or cross-sectional size of the core elements can also be provided in sizes that increase in preselected increments, such as, for example, 6 mm, 8 mm, 10 mm, etc., diameters.

In reference to FIGS. 1-4, and 6-11, the sleeve elements 120 are preferably expandable. The sleeve elements 120 preferably have an opening at the distal end that communicates with a hollow interior. The sleeve elements also preferably have an opening at the proximal end in communication with the hollow interior so that the sleeve elements are preferably hollow tubes having a length, an inside diameter DI, a shell thickness t and an outside diameter DO. The proximal end of the sleeve element may not have an opening and may be closed, partially closed, partially open and/or formed with a lip, flange or shoulder that partially obstructs the proximal opening and may form a stop member that prevents the sleeve from being inserted too far over the core element. The sleeve elements and core element are preferably configured such that the diameter or cross section of the exterior surface 117 of the core element 110 is approximately the same size or slightly larger than the inside diameter DI or cross-section of the sleeve member so that preferably the sleeve element has to expand slightly to fit over the core element. In this manner a compressive radial force is applied against the core element by the sleeve element to assist in securing the sleeve element to the core element.

In reference to FIGS. 1-4 and 6-11, the sleeve elements may include a plurality of ribs 122 and spacers 124. Ribs 122 and spacers 124 are preferably formed of any biocompatible material of sufficient structural integrity and strength to support physiological loads applied there across. Such materials may include, for example, stainless steel, titanium, titanium alloys, metals, metal alloys, ceramics, polymers, PEEK, composite materials, allograft or autograft bone. The ribs 122 and spacers 124 may be interconnected by an expandable membrane 126 or mesh formed of a metal, polymer or elastomeric material. The expandable membrane 126 is attached to the ribs 122 and spacers 124 to apply an inward radial compressive force. The membrane 126 may be attached to any surface of the ribs 122 or the spacers 124 or pass through the bodies of the ribs 122 and the spacers 124. The membrane 126 may be a uniform element, or comprised of segmental portions that interdigitate between the ribs 122 and the spacers 124. The membrane 126 may permit uniform or variable expansion between the ribs 122 and spacers 124 in order to best fill voids in bone and support loading. One or more expandable membranes 126 may be provided with the sleeve elements 120. Expandable membranes 126 may be present in addition to, or alternatively in place of, expandable bands 136.

The sleeve element 120 may also comprise ribs and spacers interconnected by flexible struts that extend between each rib and spacer. The flexible struts permit expansion between the ribs and spacers. The sleeve element may be a one piece integral design of the ribs, spacers and struts and may be machined from a single piece of material. The flexible struts may permit controlled expansion between each rib and spacer to permit non-uniform expansion and result in a non-circular cross-sectional shape that may have at least one flat surface or side. Having a flat side or surface may be advantageous in certain procedures, such as, for example, expanding vertebral bone where the flat surface can be oriented to be parallel to the end plates of the vertebra to apply pressure to reorient, expand and support the vertebra end plates.

Figure 7:
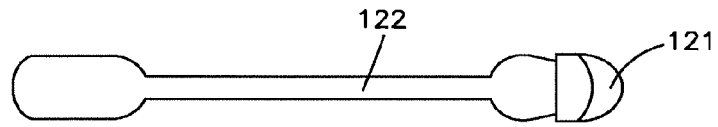
FIGS. 7 and 8 respectively illustrates a top elevation view of a rib and a spacer of the sleeve element.
Figure 8:
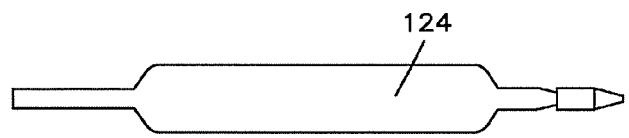

The ribs 122 may have dog bone shape as illustrated in FIG. 7 or any other suitable shape. The spacers 124 may have the shape illustrated in FIG. 8 or any other suitable shape. The ribs and spacers may have shapes that correspond and compliment each other as shown, or non-corresponding, non-complimentary shapes. The sleeve element is formed of numerous ribs 122 and spacers 124 to preferably permit the sleeve to be flexible and expandable. The sleeve also may be formed of only ribs or only spacers, each having substantially the same size and shape, or same shape but different sizes.

The sleeve elements 120 may be approximately 1 mm in thickness, although other thickness are contemplated. The thickness of the sleeve elements, the ribs and the spacers may have a relatively uniform thickness, and may be relatively flat. Alternatively, the sleeves, ribs and spacers may have a relatively non uniform thickness, and may be, for example, wedge shaped. Alternatively, or additionally, the exterior surface of the sleeves, rib or spacer may be curved, as well as the internal surface. The exterior surface 128 of the sleeve element may have a recess 139 while the interior surface 129 may have a projection 138. The projection 138 on the sleeve element 120 will preferably engage and interlock with the recess 119 formed in the core element 110, or the recess 139 formed in an adjacent sleeve element 120. The projections 138 and recesses 139 may be formed on the ribs 122, the spacers 124 or both. The projections 138 and recesses 139 may extend only partially across the width of, or the entire width of, the ribs and spacers. The projections 138 preferably will snap fit into the recesses 119, or recesses 139. In this manner, the expandable sleeve elements are coupled to the core element and preceding sleeve elements to provide a structurally integrated implant to support loads experienced in bones or other tissue.

Figure 4:
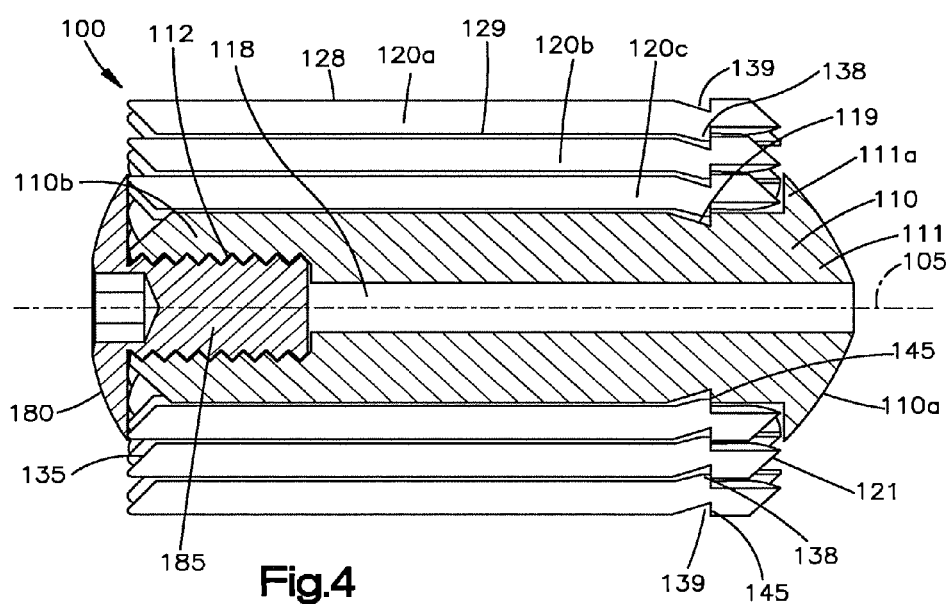
FIG. 4 illustrates a cross sectional side view of the expandable implant of FIG. 1.
Figure 6:
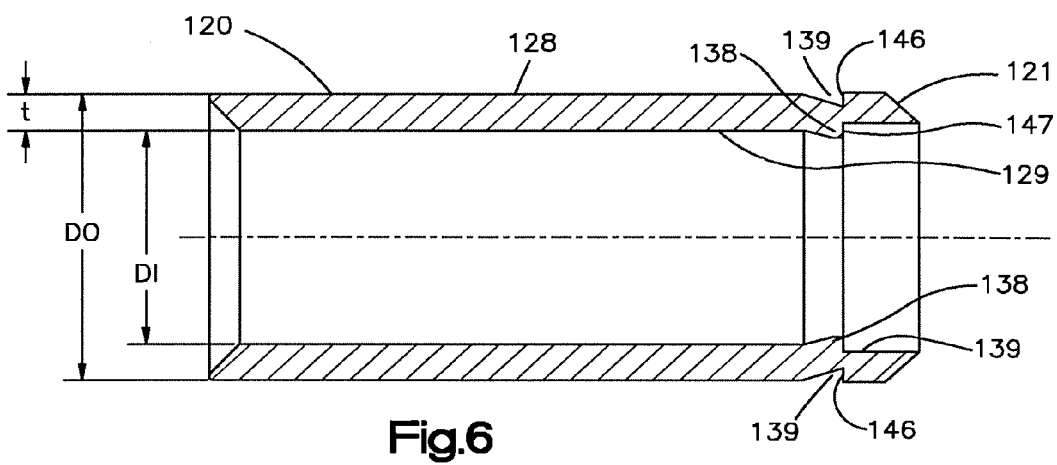
FIG. 6 illustrates a cross sectional view of a sleeve element of the expandable implant shown in FIGS. 1-4.

The recesses 119 and 139 and corresponding projections 138 may be triangularly shaped as illustrated in FIGS. 4-6 to facilitate the projections 138 sliding into the recesses 119, 139 as the sleeves move over the core element. The shape of the distal portion or wall 146 of the recesses 119, 139, and the wall 147 on the projections 138 preferably form a stop mechanism 145 to prevent the sleeve element from extending beyond the core element or previously placed sleeve elements. Features may be provided in the recesses 119, 139 and the projections 138 to facilitate the locking of the sleeve element to the core element, or the preceding sleeve element. The projections and recesses on the core element and sleeve elements may be reversed so that a projection is formed on the exterior surface of the core element and/or sleeve element, and recesses are formed on the interior surfaces of the sleeve elements. The recesses and projections may be triangularly shaped with a wall substantially perpendicular to the length of the core element and/or sleeve element as illustrated in FIG. 4, or other shapes may be utilized.

Alternatively or additionally, other features may be provided on the core element and sleeve element to couple the sleeve elements to each other, or the core element. For example, as shown in FIG. 10, the sleeve and core element may be provided with a bump 150, preferably rounded, just distal of the recess 119, 139; and a dimple 152, preferably rounded, just distal of the projection 138, to receive the bump to assist in engaging the sleeve to the core element.

The implant 100 may be inserted via an insertion instrument. As best shown in FIG. 9, a preferred embodiment of the insertion instrument 200 is shown. The insertion instrument 200 is preferably configured for use with the implant 100 and may be specifically adapted for a minimally invasive surgical method. The instrument 200 preferably includes a hollow barrel 210 and a rod 220 preferably centered radially within the barrel 210. The rod 220 includes a core element engagement feature 225 at its distal end, such as, for example, exterior threading or a star drive, capable of mating with the instrument engagement feature 115 on the core element 110. The sleeve elements 120 are preferably housed along the rod 220 in end-to-end fashion and are capable of being advanced through the barrel 210 and along the rod 210. In one embodiment, the instrument 200 is used to direct and place the core element 110 within bone, preferably a collapsed vertebral body. Sleeves 120 are passed through the barrel 210 and along the rod 220 and over the implanted core element 110 as discussed above, such as by a plunging mechanism 230. The interior of the sleeves 120, preferably the interior of the distal ends of the sleeves 120, can be configured to snap onto the distal end of core element 110 to secure the sleeve 120 to core element 110, or to secure sleeve 120a to sleeve 120b, etc. When the surgeon has obtained the desired radial volume or size of the expandable implant 100, the surgeon stops advancing additional sleeves 120 and releases the engagement feature 225 from the engagement feature 115.

Referring to FIGS. 1, 4 and 6, in a preferred embodiment, the sleeves 120 preferably include a ramped nose 121 at their distal end that permits or facilitates the sleeve 120 that is being inserted or urged onto core element 110, after another sleeve 120 is already positioned on the core element 110, to radially expand the sleeve or sleeves 120 already positioned on the implant to accommodate the new sleeve 120. The ramped nose 121 on the distal end of the sleeve 120 is not limited to the shape shown and the sleeves 120 may be arranged and shaped in nearly any manner, or the rod 220 may be constructed in nearly any manner to permit the sleeves 120 to radially expand as additional sleeves 120 are inserted onto the distal end of the core element. For example, each of the sleeves 120 may include a ramp 135 that is angled opposite of the ramped nose 121 to accommodate one sleeve 120 sliding beneath another sleeve 120 and onto the core element 110. The ramped nose 121 on the sleeve 120 may also facilitate the sleeve sliding underneath the expandable bands 136, if such expandable bands 136 are provided on the core element. The presence of longitudinal grooves in the core element may also facilitate the sliding and alignment of the sleeve elements on the core element and each other, and the longitudinal grooves may further assist and facilitate the sleeves sliding underneath the expandable bands 136.

The sleeves 120 may be provided preloaded in the insertion instrument. Alternatively, the sleeves may be selected and loaded just prior to insertion into the patient, for example, in the operating room, or just prior to the procedure, by the doctor surgeon or staff workers. The sleeves may be supplied in a variety of lengths and thicknesses. In one exemplary embodiment, the sleeve may be approximately 18 mm long, an inside diameter of approximately 5.5 mm and a shell thickness t of approximately 1 mm so that each additional sleeve increases the thickness, height, diameter or cross sectional size of the expandable implant 100 by approximately 2 mm. For example, the expandable implant in FIG. 1 having a core element diameter of approximately 6 mm, and three expandable sleeves of approximately 1 mm in thickness would have a diameter of between approximately 12 and 13 mm when accounting for the spacing and gaps between the sleeves. The sleeves may also be provided in different lengths, and numerous sleeves of different lengths may be provided in a kit or system in order to form expandable implants of different lengths and heights.

The insertion instrument may be loaded with multiple sleeves all having the same size and configuration of ribs and spacers resulting in sleeves, in the unexpanded condition, of the same size (length and diameter). As the same sized sleeves are inserted over the core, the earlier placed sleeves will expand such that each respective stacked sleeve in the expanded condition will be a different diameter (cross-sectional size). In the expandable implant, the first placed expandable sleeve will radially expand the most, and the spacing between the ribs and spaces will be larger on the first sleeve member. That is, the spacing between the ribs and spacers after insertion on the core element will vary by the level of the stacked sleeve. In the embodiment of FIG. 1 the gap or space between each rib and spacer will be about 0.45 mm in the second row and about 0.58 mm in the third row. Alternatively, different sized sleeves (length and/or diameter) can be loaded into the insertion instrument. If different length sleeves are used to construct the expandable implant, the sleeves can be constructed so that as they are stacked the distal end provides a tapered or blunt distal end. For example, the sleeves can be constructed so that the recesses 139 and projections 138 are configured so that the distal end beyond the projection on each subsequently inserted sleeve is the same length or longer than each previously inserted sleeve.

Figure 11:
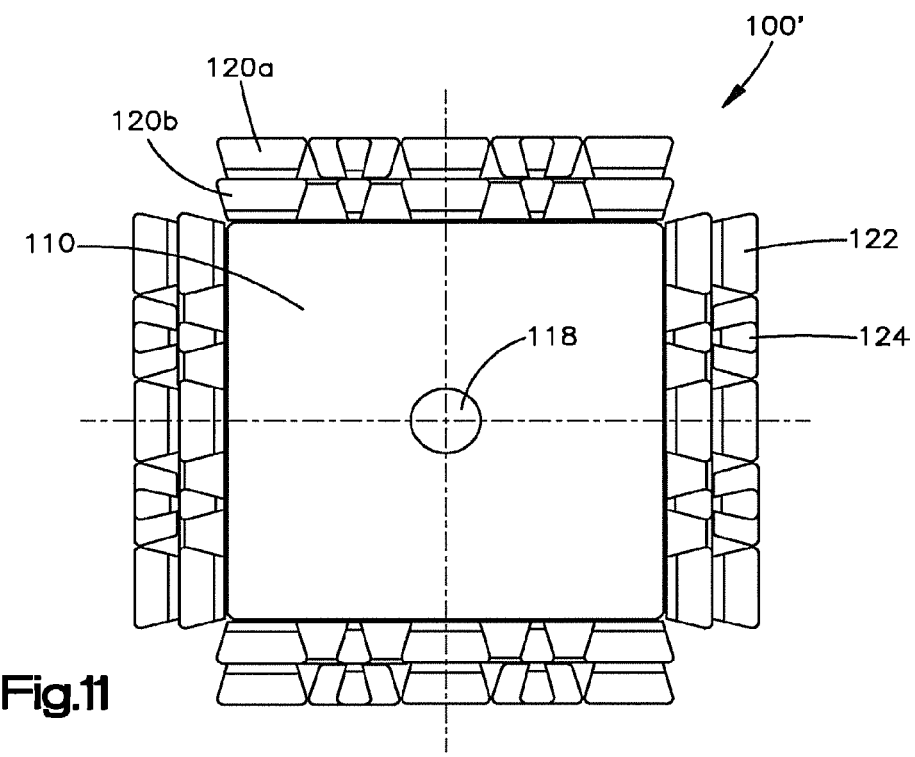
FIG. 11 illustrates a cross-sectional view of the expandable implant of FIG. 10.
Figure 12:
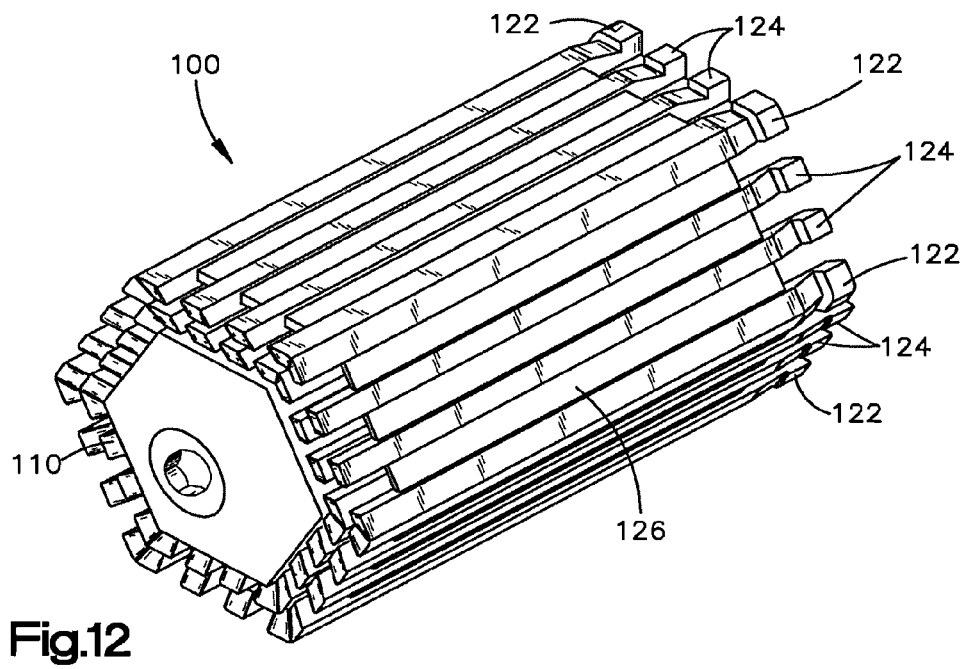
FIG. 12 illustrates a front top perspective view of another embodiment of an expandable implant in accordance with the present invention.
Figure 13:
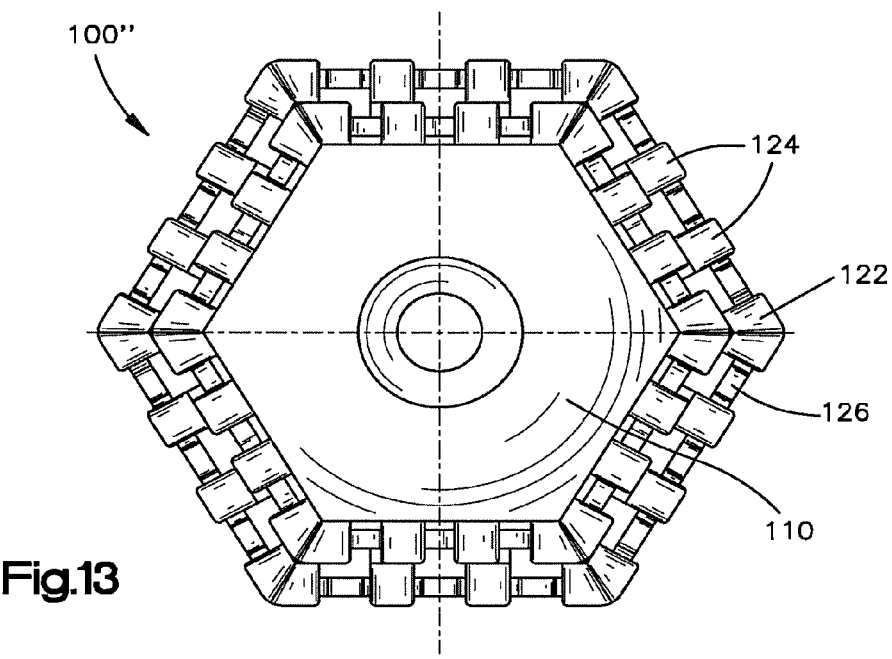
FIG. 13 illustrates a front elevation view of the expandable implant of FIG. 12.
Figure 14:
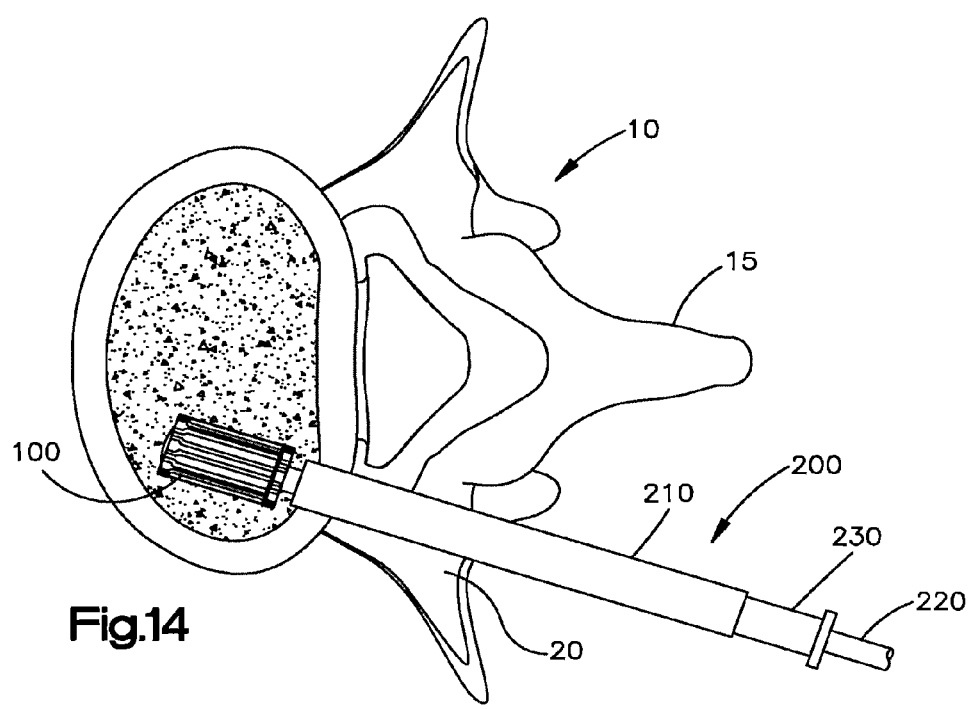
FIG. 14 illustrates a view of one embodiment of the expandable implant inserted into a vertebral body.

It may be advantageous in certain bone or in certain conditions that a non-cylindrical shaped implant be provided. For example, it may be advantageous to provide an expandable implant that has a relatively flat surface. Such flat surfaces may be advantageous in vertebral bodies where the flat surface or surfaces can be directed toward the inferior or superior end plates of the vertebral body. Such shapes may be advantageous in long bones and other bones as well. Non-cylindrical implant shapes contemplated include hexagonal, octagonal, square, trapezoidal, other polygonal shapes or asymmetrical shapes that may provide at least one relatively flat side or surface. FIGS. 10-11 show an expandable implant forming a square shape; while FIGS. 12-13 show a hexagonally shaped implant having eight relatively flat sides. The expandable implant 100" in FIGS. 12-13 are formed with two spacers 124 on each side of the hexagon with ribs 122 on the side edges. Elastic membrane 126 connects the ribs and spacers together and permits expansion of the sleeves.

Non-cylindrical implants may be constructed or assembled with a non-cylindrical shaped core element that has at least one substantially flat side or surface. Unexpanded cylindrically shaped sleeves may be placed over the non-cylindrically shaped core element. The expansion between the ribs and spaces may vary as the sleeve expands and changes to a non-cylindrical shape. The flexible struts between the ribs and spacers would expand more in some locations than in others, or the expandable membranes or expandable bands between some ribs and spacers would expand more than in others. Alternatively the sleeve may be provided in a non-cylindrical shape where the spacing between the ribs and spacers already varies so that the sleeve is formed in a desired non-cylindrical shape. Alternatively, the sleeve elements can be formed of ribs and spacers that do not extend around the entire circumference of the sleeve. As the sleeves are placed over the core element an asymmetrical implant may be created. Alternatively or additionally, non-uniform thick ribs and spacers, and/or curved exterior and interior surfaces on the ribs and spacers may be used to create the desired shape and size of the expandable implant.

In use, a passageway is created to the bone to be treated and a passage may be made into the bone where the implant is to be located. A drill or trocar may be used to create the passage into the bone. Optionally, a cavity may be formed in the bone by removing or compacting bone, preferably cancellous bone. A balloon expandable catheter may be used to create the cavity, or other instruments may be used to create the cavity by compacting bone or removing bone. Alternatively, only the passage may be formed in bone without forming an enlarged cavity. An access tube or cannula may be inserted down through the soft tissue. The access tube also may be inserted into the passage in the bone. The access tube preferably has a sufficient inside diameter (cross-section) to permit the insertion instrument and core element down the hollow bore provided in the access tube.

The core element is preferably attached to (threaded onto) the rod of the insertion instrument. The insertion instrument can be preloaded with sleeves prior to or after attachment of the rod to the core element. The insertion instrument and core element assembly together may be inserted down the access tube and the core element placed in position in the passage or cavity in the bone.

The plunger mechanism is activated to move the first sleeve 120a over and onto the core element while the rod and barrel of the insertion instrument remains stationary in the bone. If further expansion of the implant is desired the plunger mechanism is operated to move the second sleeve 120b over the core element and under the first sleeve 120a to provide an implant with a larger diameter or cross-sectional size. If yet further expansion of the implant is desired the plunger mechanism is operated again to place a third sleeve 120c over the core element and under the second sleeve 120b to provide a still larger sized implant of increased diameter, or cross-sectional size (height and/or thickness). Placing additional sleeves 120 over the core element is continued until the implant is the desired size. As subsequent sleeves are inserted, the earlier inserted sleeves expand. The expanding of the sleeves and thus the implant can fill the cavity created in the bone, or other tissue, or a space. Expanding of the sleeves and the implant may additionally compact bone, preferably cancellous bone, depending upon the treatment desired. The expanding of the implant may also move bone and/or tissue. In one preferred embodiment the expanding of the implant may compact cancellous bone and move cortical bone to restore or place the bone into its desired size, shape and position. For example, the implant may move or compact cancellous bone in a vertebral body, and may further move the vertebral endplates to adjust the height and angle of the endplates.

After the implant is expanded to the desired size, the rod is detached from the implant. Optionally, end cap 180 can be coupled to the proximal end 110b of the implant 100. The end cap 180 may have a projection 185 that extends into the bore 118a of the core element. The projection 185 may have threading to engage the threading in the core element, or may simply snap fit into the bore 118a by a flange (not shown) and shoulder (not shown). Other ways of connecting end cap 180 to the implant 100 are contemplated. Different size end caps 180 may be provided so that the end cap may extend radially beyond the core element and prevent the sleeves from moving distally.

While the core element and insertion instrument have been described as being inserted down an access tube, it will be appreciated that the insertion instrument and core member may be inserted directly through the skin without tissue retractors or cannulas, or can puncture the skin directly, and additionally or alternatively, may be inserted over a guide wire into position.

Once the implant is positioned it may be drilled and tapped from any direction to pass screws, nails, k-wires or other fasteners to supplement the fixation with other hardware. For example, if placed in a vertebral body, the sleeve implant can assist with plate fixation by having the sleeve drilled and tapped to receive one or more screws which are inserted into the vertebrae to fix the vertebral plate in position. The same procedure of using the sleeve implant to supplement plate fixation can be used in long bones, soft tissues or non-medical applications.

Furthermore, after the implant 100 is placed in bone, bone cement, bone chips or other biological material or polymeric material may be inserted into the cavity or passage in the bone. Additionally, or alternatively, a plug, for example, formed of bone, may be inserted behind the implant 100. The bone cement or other biologic or polymeric materials may be used in conjunction with the supplemental fixation discussed above and may be inserted before, after or during the supplemental fixation.

The implant 100 and preferred minimally invasive surgical method provided by the present invention enables a surgeon to control the original position and final expansion geometry of the implant 100 because the implant 100 expands geometrically.

In one embodiment, the core element has a diameter or height of approximately 4 mm to approximately 8 mm and a length of approximately 1.5 cm to approximately 2.5 cm, and the sleeve elements have an inside diameter or height of approximately 4 mm to approximately 8 mm, and a length of approximately 1.5 cm to approximately 2.5 cm, and a thickness of approximately 1 mm to approximately 2 mm. Of course, different size core elements and sleeves may be provided as it will be appreciated that different size implants will be appropriate and desirable depending upon the application, including, for example, the bone being treated. One of skill in the art will know and appreciate the size of the implant, core elements and sleeves appropriate for the different bone, fractures and conditions being treated.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention.

What is claimed:
1. A kit configured to form an expandable implant for treating bone, the kit comprising:
   a core element including a core body that defines a proximal end and a distal end spaced from the proximal end along a first direction, the core element further including a stop that extends radially out from the core body proxi- mate to the distal end, the core defining a core thickness along a second direction that is perpendicular to the first direction; and a plurality of radially expandable sleeves configured to be sequentially insertable over the core element along the first direction in such a manner that each of the plurality of expandable sleeves is configured to overlay another one of the plurality of expandable sleeves with respect to the second direction so as to form the expandable implant, each of the plurality of expandable sleeves defining a fixed thickness along the second direction, wherein the stop is configured to limit insertion of one or more of the plurality of expandable sleeves along the first direction relative to the core element.

2. The kit of claim 1, wherein the plurality of radially expandable sleeves are configured to be sequentially insertable over the core element along the first direction in such a manner that a first sleeve of the plurality of radially expandable sleeves is inserted over the core element and each subsequently inserted sleeve is received between the core element and the previously inserted sleeve such that the insertion of each additional sleeve causes each previously inserted sleeve to outwardly expand.

3. The kit of claim 1, wherein the core body defines at least one mating feature and each radially expandable sleeve defines at least one mating feature such that the mating features of the core body and the sleeves interdigitate with each other to thereby form the expandable implant.

4. The kit of claim 3, wherein the mating features of the core body and the radially expandable sleeves are one of a projection and a recess that is configured to receive one of the projections so that the radially expandable sleeves interdigitate with each other and the core element.

5. The kit of claim 4, wherein (i) the mating feature of the core body is a recess, and (ii) each radially expandable sleeve defines a projection and a recess that is configured to receive a projection of a subsequent radially expandable sleeve.

6. The kit of claim 1, wherein each radially expandable sleeve is a one piece integral unit formed of a plurality of ribs that are elongate along the first direction, a plurality of spacers that are elongate along the first direction, and a plurality of flexible struts that connect adjacent ribs and spacers to each other.

7. The kit of claim 1 further comprising an end cap attachable to the proximal end of the core body, the end cap being configured to prevent at least the radially expandable sleeve that is adjacent the core element from moving along a direction that is opposite the first direction when the end cap is attached to the core body.

8. The kit of claim 7, wherein the proximal end of the core element defines a threaded bore and the end cap includes a threaded projection that is configured to be received by the bore to thereby attach the end cap to the core element.

9. The kit of claim 1 wherein the radially expandable sleeves initially have a cylindrical shape and are expandable to a non-cylindrical shape.

10. The kit of claim 1, wherein the expandable implant has a thickness that expands with respect to the core thickness an amount equal to a sum of the fixed thicknesses of each of the radially expandable sleeves that are sequentially inserted over the core element.

11. A system for treating bone, the system comprising:
a rigid core element having an instrument engagement feature, the core defining a proximal end and a distal end spaced from the proximal end along a first direction;
an insertion instrument that includes a rod element having a core element engagement feature that is configured to mate with the instrument engagement feature to thereby selectably couple the core element to the insertion instrument; and
a plurality of expandable sleeves that are configured to be advanced along the rod element and onto the core element, in such a manner that each of the plurality of expandable sleeves is configured to overlay another one of the plurality of expandable sleeves along the core element with respect to a second direction that is perpendicular to the first direction.

12. The system of claim 11, wherein the insertion instrument further includes a cannulated barrel and wherein the rod element is disposed within the cannulated barrel.

13. The system of claim 12, wherein (i) the expandable sleeves are configured to be placed in end-to-end fashion along the rod element and within the cannulated barrel such that the expandable sleeves are advanceable along the rod element and onto the core element, and (ii) advancement of at least one additional expandable sleeve element along the rod element and between the core element and a previously inserted expandable sleeve causes the previously inserted expandable sleeve to radially expand such that the radius of the implant increases as each additional expandable sleeve is applied about the core element.

14. The system of claim 11, wherein the expandable sleeves have an expandable condition and an unexpanded condition wherein in the unexpanded condition the sleeve elements are substantially cylindrically shaped and in the expanded condition the sleeves are non-cylindrically shaped.

15. The system of claim 14, wherein the expandable sleeves are configured to interdigitate with one another when the expandable sleeves are stacked on top of each other.

16. A method of treating bone in a minimally invasive manner, the method comprising the steps of:
inserting a core element that is attached to a rod element of an insertion instrument into a cavity defined by the bone;
advancing a first expandable sleeve along the rod element and onto the core element; and
advancing at least one additional expandable sleeve along the rod element and onto the core element between the core element and the previously inserted expandable sleeve, thereby causing radial expansion of the previously inserted expandable sleeve.

17. The method of claim 16, further comprising the step of attaching the core element to the rod element prior to inserting the core element into the cavity.

18. The method of claim 16, further comprising the step of inserting an access tube into soft tissue such that the access tube defines a passageway to the cavity, wherein the inserting step comprises moving the core element through the passageway.

19. The method of claim 16, further comprising the step of detaching the rod element from the core element.

20. The method of claim 19, further comprising the step of attaching a cap to the core element after the rod element has been detached to thereby lock the expandable sleeves on the core element.

* * * * *